(12) United States Patent
Chen et al.

(10) Patent No.: US 12,373,937 B2
(45) Date of Patent: Jul. 29, 2025

(54) CREEPAGE STAGE DETERMINATION SYSTEMS AND METHODS FOR ALUMINUM-CONTAINING HEAT-RESISTANT ALLOY FURNACE TUBES

(71) Applicants: HEFEI GENERAL MACHINERY RESEARCH INSTITUTE CO., LTD., Anhui (CN); SPECIAL EQUIPMENT INSPECTION STATION OF HEFEI GENERAL MACHINERY RESEARCH INSTITUTE CO., LTD., Anhui (CN)

(72) Inventors: Tao Chen, Hefei (CN); Xiaoming Lian, Hefei (CN); Zhichao Fan, Hefei (CN)

(73) Assignees: HEFEI GENERAL MACHINERY RESEARCH INSTITUTE CO., LTD., Hefei (CN); SPECIAL EQUIPMENT INSPECTION STATION OF HEFEI GENERAL MACHINERY RESEARCH INSTITUTE CO., LTD., Hefei (CN)

(*) Notice: Subject to any disclaimer, the term of this patent is extended or adjusted under 35 U.S.C. 154(b) by 0 days.

(21) Appl. No.: 19/093,217

(22) Filed: Mar. 27, 2025

(65) Prior Publication Data

US 2025/0225641 A1 Jul. 10, 2025

Related U.S. Application Data

(63) Continuation-in-part of application No. PCT/CN2024/118709, filed on Sep. 13, 2024.

(30) Foreign Application Priority Data

Dec. 28, 2023 (CN) .......................... 202311836085.2

(51) Int. Cl.
  *G06T 7/00* (2017.01)
  *G01N 21/88* (2006.01)
  *G01N 21/95* (2006.01)
  *G01N 33/2045* (2019.01)
  *G06T 7/60* (2017.01)

(52) U.S. Cl.
  CPC ....... *G06T 7/0006* (2013.01); *G01N 21/8851* (2013.01); *G01N 21/95* (2013.01);
  (Continued)

(58) Field of Classification Search
  CPC ......... G06T 7/0006; G06T 2207/10056; G06T 2207/30136; G06T 7/60; G01N 21/8851; G01N 33/2045; G01N 2021/8887
  See application file for complete search history.

(56) References Cited

U.S. PATENT DOCUMENTS 7,810,385 B1 * 10/2010 Narcus ............... G01M 15/14
  73/112.01
2015/0377757 A1 * 12/2015 Ali ......................... G01N 3/18
  73/826
2025/0066896 A1 * 2/2025 Hattendorf ............... C22F 1/10

FOREIGN PATENT DOCUMENTS

CN 105910921 A 8/2016
CN 113533674 A 10/2021
(Continued)

OTHER PUBLICATIONS

Van Rooyen M, Becker T, Westraadt J, Marx G. Creep Damage Assessment of EX-Service 12% Cr Power Plant Steel Using Digital Image Correlation and Quantitative Microstructural Evaluation. Materials (Basel). Sep. 24, 2019;12(19):3106. doi: 10.3390/ma12193106. (Year: 2019).*

(Continued)

*Primary Examiner* — Michael Robert Cammarata
(74) *Attorney, Agent, or Firm* — Porus IP LLC

(57) ABSTRACT

Creep stage determination system and method for aluminum-containing heat-resistant alloy furnace tube, the system (Continued)

includes: a micro-imaging unit, a display unit, a memory, and a processor, the micro-imaging unit configured to image specimen, the display unit configured to display a microstructure photograph of the specimen, the micro-imaging unit, the display unit, the memory and the processor are communicatively connected, and the processor is configured to: acquire at least one field-of-view image; for the field-of-view image, carry out image recognition on the field-of-view image to determine an eigenvalue of the field-of-view image; based on the eigenvalue of the at least one field-of-view image, determine a target creep value by a generative model; determine, based on the target creep value, the creep stage; and send the at least one field-of-view image and the creep stage to the display unit to display the at least one field-of-view image and the creep stage.

6 Claims, 8 Drawing Sheets

(52) U.S. Cl.
CPC ........... *G01N 33/2045* (2019.01); *G06T 7/60* (2013.01); *G01N 2021/8887* (2013.01); *G06T 2207/10056* (2013.01); *G06T 2207/30136* (2013.01)

(56) References Cited

FOREIGN PATENT DOCUMENTS

| | | | | |
|---|---|---|---|---|
| CN | 115470721 | A | | 12/2022 |
| CN | 115684161 | A | | 2/2023 |
| CN | 117969504 | A | | 5/2024 |
| CN | 118225761 | A | * | 6/2024 |
| CN | 118464603 | A | * | 8/2024 |
| JP | H0634625 | A | | 2/1994 |
| JP | H0943128 | A | | 2/1997 |
| JP | 2013134132 | A | * | 7/2013 |
| WO | WO-2024126935 | A1 | * | 6/2024 |

OTHER PUBLICATIONS

Dessolier, Thibaut, et al. "Effect of high temperature service on the complex through-wall microstructure of centrifugally cast HP40 reformer tube." Materials Characterization 177 (2021): 111070. (Year: 2021).*
International Search Report in PCT/CN2024/118709 mailed on Jan. 8, 2025, 9 pages.
Written Opinion in PCT/CN2024/118709 mailed on Jan. 8, 2025, 12 pages.

* cited by examiner

CREEPAGE STAGE DETERMINATION SYSTEMS AND METHODS FOR ALUMINUM-CONTAINING HEAT-RESISTANT ALLOY FURNACE TUBES

CROSS-REFERENCE TO RELATED APPLICATIONS

This application is a continuation-in-part application of International Application No. PCT/CN2024/118709 filed on Sep. 13, 2024, which claims priority to Chinese Patent Application No. 202311836085.2, filed on Dec. 28, 2023, the entire contents of each of which are hereby incorporated by reference.

TECHNICAL FIELD

The present disclosure relates to the field of ethylene cracking furnace tube inspection, and in particular, relates to a creep stage determination system and method for an aluminum-containing heat-resistant alloy furnace tube (27Cr44Ni5W3Al+microalloy).

BACKGROUND

The core equipment of the petrochemical ethylene plant is the ethylene cracking furnace, and the furnace tube of the ethylene cracking furnace is generally manufactured by centrifugal casting using heat-resistant alloy materials. The furnace tube is in service at high temperature, the highest wall temperature of which can reach 1100° C. In the long-term operation process of the ethylene cracking furnace, high-temperature creep is one of the main creep damage mechanisms of the furnace tube. Therefore, it is hoped to provide a creep stage determination system and method for an aluminum-containing heat-resistant alloy furnace tube, which is able to better determine the creep stage of the aluminum-containing heat-resistant alloy furnace tube.

SUMMARY

One or more embodiments of the present disclosure provide a creep stage determination system for an aluminum-containing heat-resistant alloy furnace tube, wherein the system comprises a micro-imaging unit, a display unit, a memory, and a processor, wherein the micro-imaging unit is configured to image a specimen, the display unit is configured to display a microstructure photograph of the specimen, the micro-imaging unit, the display unit, the memory, and the processor are communicatively connected, and the processor is configured to: acquire at least one field-of-view image based on the micro-imaging unit, the at least one field-of-view image being the microstructure photograph of at least one field of view; perform an image recognition on the at least one field-of-view image, and determine an eigenvalue of the at least one field-of-view image, the eigenvalue comprising at least one of a field-of-view area, a first area of an $M_{23}C_6$-type carbide and a $Ni_3Al$ phase of a peripheral lumpy precipitate in an austenitic grain boundary precipitate of a furnace tube material, a second area of an $M_7C_3$-type carbide of an internal thin strip-like precipitate in the austenitic grain boundary precipitate of the furnace tube material, and an aspect ratio of the $M_7C_3$-type carbide of the internal thin strip-like precipitate in the austenitic grain boundary precipitate of the furnace tube material; obtain a generative model from the memory; determine a target creep value based on the eigenvalue of the at least one field-of-view image by the generative model; determine the creep stage based on the target creep value; and send the at least one field-of-view image and the creep stage to the display unit to cause the display unit to display the at least one field-of-view image and the creep stage.

One or more embodiments of the present disclosure provide a method for determining a creep stage for an aluminum-containing heat-resistant alloy furnace tube, wherein the method comprises: acquiring at least one field-of-view image based on a micro-imaging unit, the at least one field-of-view image being a microstructure photograph of at least one field of view; performing an image recognition on the at least one field-of-view image, and determining an eigenvalue of the at least one field-of-view image, the eigenvalue comprising at least one of a field-of-view area, a first area of an $M_{23}C_6$-type carbide and a $Ni_3Al$ phase of a peripheral lumpy precipitate in an austenitic grain boundary precipitate of a furnace tube material, a second area of an $M_7C_3$-type carbide of an internal thin strip-like precipitate in the austenitic grain boundary precipitate of the furnace tube material, and an aspect ratio of the $M_7C_3$-type carbide of the internal thin strip-like precipitate in the austenitic grain boundary precipitate of the furnace tube material; obtaining a generative model from a memory; determining a target creep value based on the eigenvalue of the at least one field-of-view image by the generative model; determining the creep stage based on the target creep value; and sending the at least one field-of-view image and the creep stage to a display unit to cause the display unit to display the at least one field-of-view image and the creep stage.

One or more embodiments of the present disclosure provide a non-transitory computer readable medium, comprising executable instructions that, when executed by at least one processor, direct the at least one processor to perform a method, the method comprising: acquiring at least one field-of-view image based on a micro-imaging unit, the at least one field-of-view image being a microstructure photograph of at least one field of view; performing an image recognition on the at least one field-of-view image, and determining an eigenvalue of the at least one field-of-view image, the eigenvalue comprising at least one of a field-of-view area, a first area of a $M_{23}C_6$-type carbide and a $Ni_3Al$ phase of a peripheral lumpy precipitate in an austenitic grain boundary precipitate of a furnace tube material, a second area of a $M_7C_3$-type carbide of an internal thin strip-like precipitate in the austenitic grain boundary precipitate of the furnace tube material, and an aspect ratio of the $M_7C_3$-type carbide of the internal thin strip-like precipitate in the austenitic grain boundary precipitate of the furnace tube material; obtaining a generative model from a memory; determining a target creep value based on the eigenvalue of the at least one field-of-view image by the generative model; determining the creep stage based on the target creep value; and sending the at least one field-of-view image and the creep stage to the display unit to cause the display unit to display the at least one field-of-view image and the creep stage.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, wherein.

DETAILED DESCRIPTION

Figure 1:
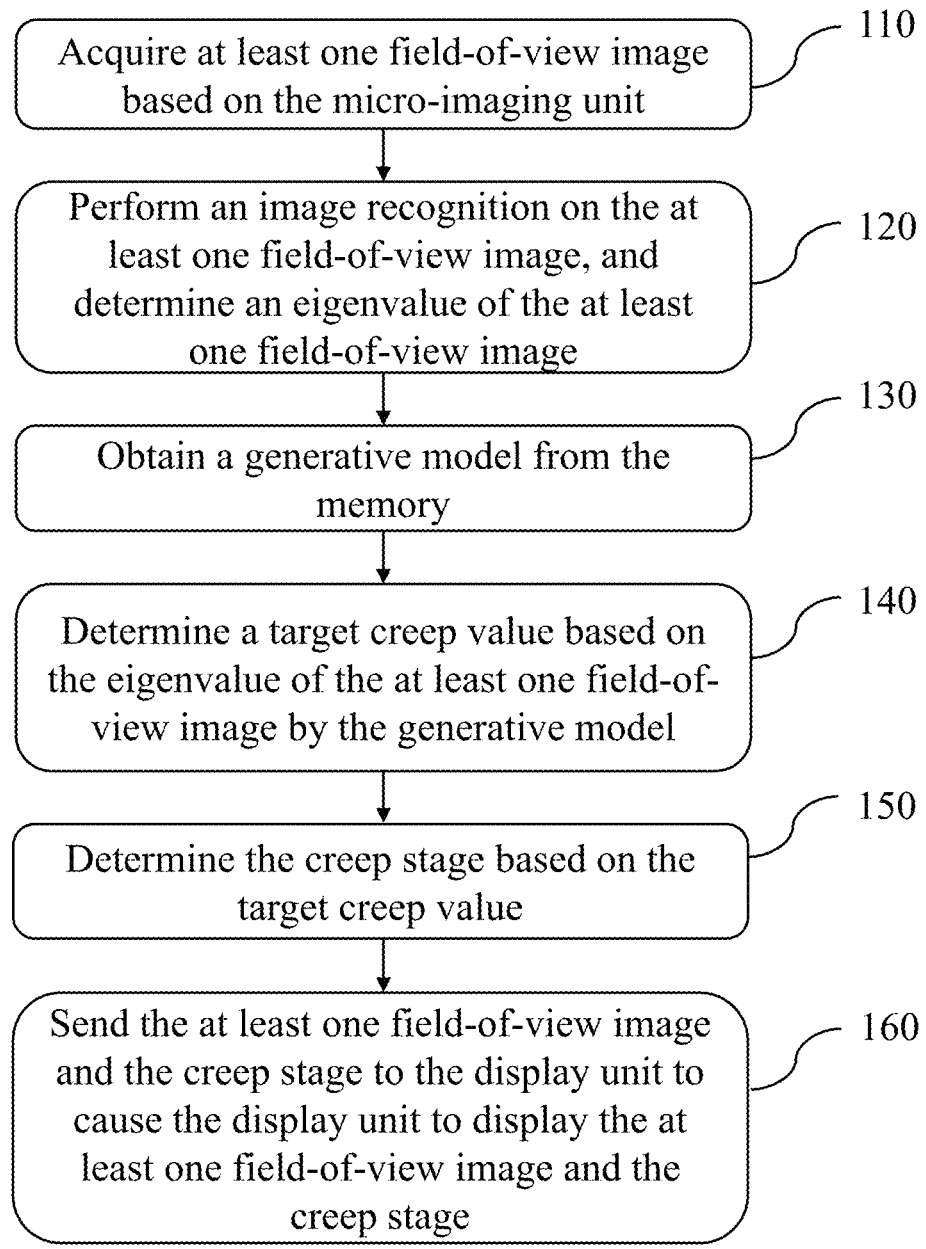
FIG. 1 is a flowchart illustrating a creep stage determination method for an aluminum-containing heat-resistant alloy furnace tube according to some embodiments of the present disclosure.

The accompanying drawings, which are required to be used in the description of the embodiments, are briefly described below. The accompanying drawings do not represent the entirety of the embodiments.

Unless the context clearly suggests an exception, the words "one", "a", "an", and/or "the" do not refer specifically to the singular, but may also include the plural. Generally, the terms "including" and "comprising" suggest only the inclusion of clearly identified steps and elements. In general, the terms "including" and "comprising" only suggest the inclusion of explicitly identified steps and elements that do not constitute an exclusive list, and the method or apparatus may also include other steps or elements.

The creep damage of heat-resistant alloy materials is generally divided into three stages: a creep first stage, a creep second stage, and a creep third phase. The creep first stage is also known as a deceleration of the creep stage, where the alloy strain rate gradually decreases with the increase in creep time and the duration of this stage generally accounts for 5% to 10% of the total creep time. The creep second stage, i.e., the steady-state creep stage, is characterized by no significant change in alloy strain rate with the increase in creep time, and the duration of this stage generally accounts for 80% to 90% of the total creep time. The creep third phase, i.e., an accelerated creep stage, is characterized by the alloy strain rate increasing rapidly with the increase in creep time until the occurrence of creep fracture, and the duration of this stage generally accounts for 5% to 10% of the total creep time.

For the ethylene cracking furnace tube, once the creep damage enters the third stage, namely the accelerated creep stage, the furnace tube material has entered the terminal stage of creep life. To ensure the long-term safe operation of the ethylene unit, it has become an urgent issue for the ethylene industry to promptly identify the creep damage state of the in-service furnace tube and determine the creep stage in which the furnace tube is, which provides technical references for planning the timing of furnace tube maintenance and replacement, ensuring safe and stable operation of the furnace tube within the maintenance cycle.

To determine the state of creep damage to the furnace tube material, the traditional method involves conducting a high-temperature creep test under certain temperature and stress conditions and using the creep time-strain rate curve for determination. However, this method has two disadvantages: 1) High-temperature creep test is conducted with a stress condition below the high-temperature yield strength of the furnace tube material, resulting in longer test cycles, which often cannot meet the short maintenance cycle requirements of ethylene units; 2) Creep tests are destructive sampling tests, requiring a relatively large amount of material for specimen processing, which causes significant damage to the body of the furnace tube.

The present disclosure provides a creep stage determination system and method for an aluminum-containing heat-resistant alloy furnace tube, which may determine the target creep value based on an eigenvalue of a field-of-view image, further determine a creep stage based on the target creep value, and display at least one field-of-view image and the creep stage. The following is an example of an aluminum-containing heat-resistant alloy furnace tube (27Cr44Ni5W3Al+microalloyed furnace tube).

During the operation of the cracking furnace, the furnace tube of the radiant section is in service at high temperature, the highest wall temperature of which reach up to 1100° C. Under the effects of high temperature and internal pressure, creep damage occurs in the 27Cr44Ni5W3Al+microalloyed furnace tube. With the increase of wall temperature and the prolongation of time, the degree of creep damage increases.

On the one hand, at the high temperature state, with the prolongation of service time, an austenitic grain boundary internal thin strip-like $M_7C_3$-type carbide is gradually transformed to a lumpy $M_{23}C_6$-type carbide, and grows up at the edge of an austenitic grain boundary precipitate, at the same time, a small amount of $Ni_3Al$ phase also precipitates between the austenite grain boundary and the lumpy $M_{23}C_6$-type carbide; On the other hand, new secondary $M_{23}C_6$-type carbide precipitated from the austenite also aggregates at the edge of the austenitic grain boundary precipitate; therefore, with the prolongation of service time, and aggravation of the creep damage, the total number of austenitic grain boundary precipitate increases, and an area of the lumpy $M_{23}C_6$-type carbide and the $Ni_3Al$ phase at the edge of the austenitic grain boundary precipitate also increases, and an area of the internal thin strip-like $M_7C_3$-type carbide of the austenite precipitate reduces, i.e., the percentage of lumpy $M_{23}C_6$-type carbide and the $Ni_3Al$ phase at the edge of the austenitic grain boundary precipitate also increases.

Figure 5:
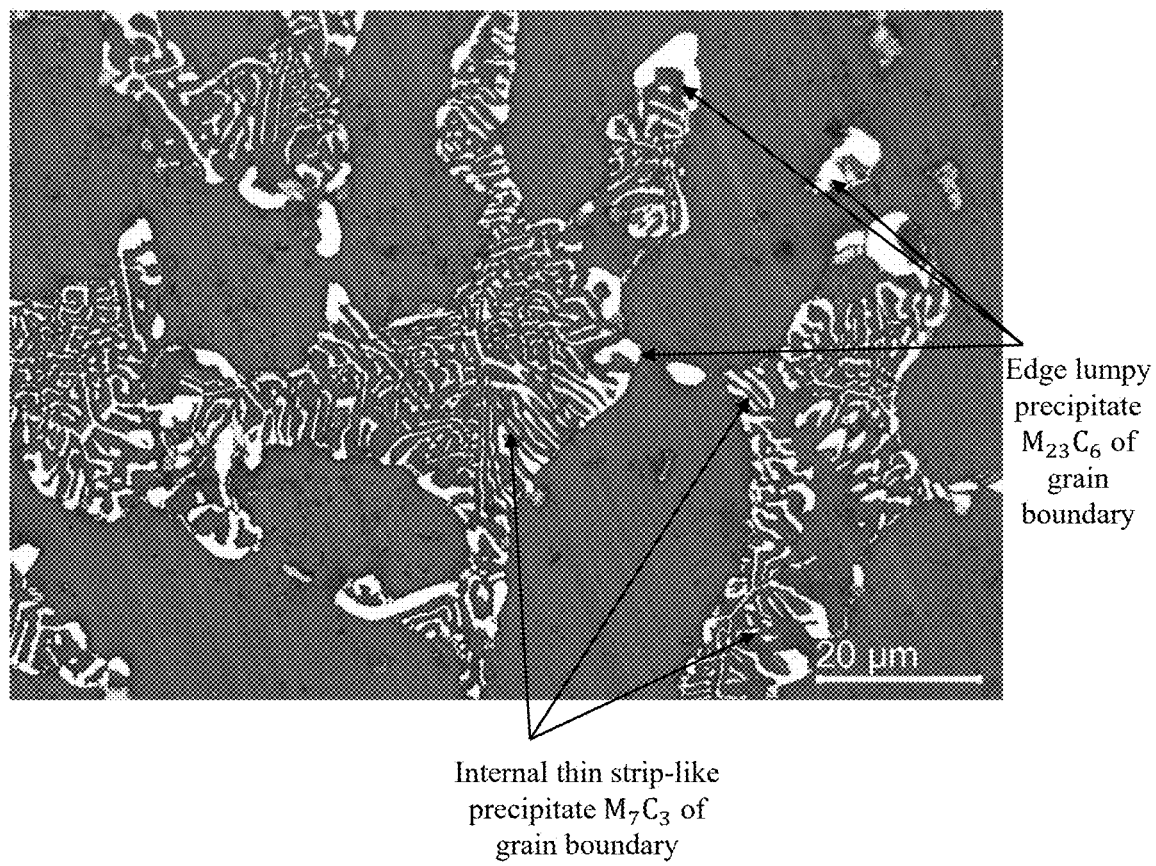
FIG. 5 is a microstructure photograph of the grain boundary and intragranular precipitates of the aluminum-containing heat-resistant alloy furnace tube according to some embodiments of the present disclosure.

For the internal thin strip-like $M_7C_3$-type carbide of the austenitic grain boundary precipitate, on the one hand, with the increase in service time at high temperature, the $M_7C_3$-type carbide is gradually transformed to the lumpy $M_{23}C_6$-type carbide; on the other hand, with the increase in a degree of creep and under the action of high temperature stress, the thin strip-like $M_7C_3$-type carbide is gradually transformed to shortening and coarsening in morphology, so an aspect ratio of the internal thin strip-like precipitate of the austenitic grain boundary precipitate is gradually reduced with the increase in a degree of the creep. The typical microstructure photographs of grain boundary and intragranular precipitates of the 27Cr44Ni5W3Al+microalloyed furnace tube are shown in FIG. 5, FIG. 5 refers to the typical microstructure photograph of grain boundary and intragranular precipitates of the 27Cr44Ni5W3Al+microalloyed furnace tube at a temperature of 1100° C. FIG. 5 shows a grain boundary internal strip-like precipitate $M_7C_3$-type carbide and a grain boundary peripheral lumpy precipitate $M_{23}C_6$-type carbide.

Figure 6:
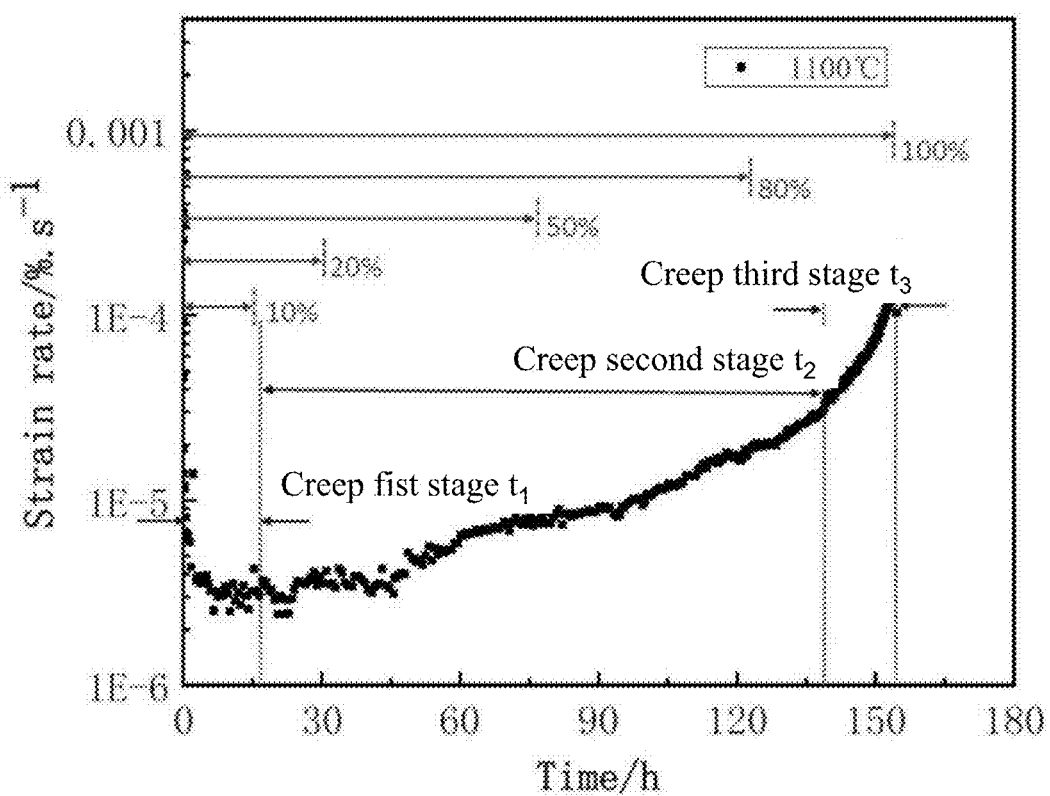
FIG. 6 is a typical creep time-strain rate curve for an aluminum-containing heat-resistant alloy furnace tube at 1100° C. and 17 MPa, which illustrates the different stages, according to some embodiments of the present disclosure.

In some embodiments of the present disclosure, the target creep value is determined based on the determined eigenvalue, which can quickly determine the creep stage in which the 27Cr44Ni5W3Al+microalloyed furnace tube, and overcome the drawbacks of time-consuming and destructive the traditional high-temperature creep test. FIG. 6 is a typical creep time-strain rate curve for an aluminum-containing heat-resistant alloy furnace tube (27Cr44Ni5W3Al+microalloyed furnace tube) at 1100° C. and 17 MPa, which illustrates the different stages, which determines the creep stage of the furnace tube and confirms that the determination method may quickly and accurately assess the creep damage state of the 27Cr44Ni5W3Al+microalloyed furnace tube, provide a basis for the time of the replacement of the furnace tube, and provide a reference for the petrochemical ethylene plant management personnel to develop maintenance strategies and ensure the safe and stable operation of the plant.

FIG. 1 is a flowchart illustrating a creep stage determination method for an aluminum-containing heat-resistant alloy furnace tube according to some embodiments of the present disclosure. As shown in FIG. 1, a process 100 includes operations 110-150 as described below. In some embodiments, the process 100 may be executed by a processor.

In some embodiments, a creep stage determination system for an aluminum-containing heat-resistant alloy furnace tube comprises a micro-imaging unit, a display unit, a memory, and a processor, wherein the micro-imaging unit is configured to image a specimen, the display unit is configured to display a microstructure photograph of the specimen, the micro-imaging unit, the display unit, the memory, and the processor are communicatively connected, and the processor is configured to: acquire at least one field-of-view image based on the micro-imaging unit, the at least one field-of-view image being the microstructure photograph of at least one field of view; perform an image recognition on the at least one field-of-view image, and determine an eigenvalue of the at least one field-of-view image, the eigenvalue comprising at least one of a field-of-view area, a first area of a $M_{23}C_6$-type carbide and a $Ni_3Al$ phase of a peripheral lumpy precipitate in an austenitic grain boundary precipitate of a furnace tube material, a second area of a $M_7C_3$-type carbide of an internal thin strip-like precipitate in the austenitic grain boundary precipitate of the furnace tube material, and an aspect ratio of the $M_7C_3$-type carbide of the internal thin strip-like precipitate in the austenitic grain boundary precipitate of the furnace tube material; obtain a generative model from the memory; determine a target creep value based on the eigenvalue of the at least one field-of-view image by the generative model; determine the creep stage based on the target creep value; and send the at least one field-of-view image and the creep stage to the display unit to cause the display unit to display the at least one field-of-view image and the creep stage.

The furnace tube refers to one of the main equipment used to carry out the cracking reaction in an ethylene cracker. The furnace tube is usually made of a high-temperature-resistant material, which is the central part for the thermal cracking reaction in the cracker. The 27Cr44Ni5W3Al+microalloyed furnace tube refers to a furnace tube made of the 27Cr44Ni5W3Al+microalloyed material.

The micro-imaging unit refers to a device configured to image the specimen. The specimen refers to a sample obtained by sampling the 27Cr44Ni5W3Al+microalloyed furnace tube. In some embodiments, the micro-imaging device may include, but is not limited to, one or more of an optical microscope, an electron microscope, or the like.

In some embodiments, the micro-imaging unit may include an Olympus® GX53 metallurgical microscope. The Olympus® GX53 metallurgical microscope has a magnification of 1000 times for the specimen.

The display unit refers to a device configured to display a microstructure photograph of a specimen. In some embodiments, the display unit may include a computer monitor, a television, a virtual reality display device, an augmented reality display device, or the like.

The memory may store data, instructions, and/or any other information. In some embodiments, the memory may store data and/or instructions related to the determination of the creep stage of the aluminum-containing heat-resistant alloy furnace tube. For example, the memory may store a generative model.

The processor refers to a device for executing or processing instructions and/or data related to the determination of the creep stage of an aluminum-containing heat-resistant alloy furnace tube. In some embodiments, the processor may be a single server or a server group. The server group may be centralized or distributed. In some embodiments, the processor may be local or remote. In some embodiments, the processor may be implemented on a cloud platform.

In some embodiments, the micro-imaging unit, the display unit, the memory, and the processor are communicatively connected.

In 110, acquire at least one field-of-view image based on the micro-imaging unit.

The field of view refers to a range that may be observed by the micro-imaging unit. In some embodiments, the field of view may be related to the field of view angle, and the larger the field of view angle, the larger the field of view, and the wider the range that the micro-imaging unit may observe.

In some embodiments, the number of at least one field of view is not less than 20.

The at least one field-of-view image refers to a microstructure image of the at least one field of view.

In some embodiments, the processor may acquire a field-of-view image via a micro-imaging unit. For example, the processor takes the microstructure image of the furnace tube through an electron microscope.

In 120, perform an image recognition on the at least one field-of-view image, and determine an eigenvalue of the at least one field-of-view image.

The eigenvalue refers to a parameter that characterizes a field-of-view image. In some embodiments, the eigenvalue may include at least one of a field-of-view area, a first area, a second area, and an aspect ratio.

The field-of-view area refers to a range of the field-of-view image that a user may acquire through the micro-imaging unit. In some embodiments, the field-of-view area may be acquired based on the parameters of the micro-imaging unit.

The first area refers to an area of the $M_{23}C_6$-type carbide and the $Ni_3Al$ phase of the peripheral lumpy precipitate in the austenitic grain boundary precipitate of the furnace tube material.

The second area is an area of the $M_7C_3$-type carbide of the internal thin strip-like precipitate in the austenitic grain boundary precipitate of the furnace tube material.

In some embodiments, the total precipitates include the $M_{23}C_6$-type carbide, the $M_7C_3$-type carbide, and the $Ni_3Al$ phase.

The aspect ratio refers to the aspect ratio of the $M_7C_3$-type carbide of the internal thin strip-like precipitate in the austenitic grain boundary precipitate of the furnace tube material.

In some embodiments, the processor may determine the first area, the second area, and the aspect ratio based on the pixel information and the field-of-view area of the image.

In some embodiments, the processor may determine the eigenvalues based on Image Pro® Plus 6.0 image analysis software. In some embodiments, when the processor determines the eigenvalues based on the Image Pro® Plus 6.0 image analysis software, a range is selected as 10, a thresh is selected as 3, a smooth is selected as 1, and a speed is selected as 2.

In some embodiments of the present disclosure, determining the eigenvalues by the Image Pro® Plus 6.0 image analysis software facilitates a more accurate analysis of the field-of-view image, which in turn improves the work efficiency.

In 130, obtain the generative model from the memory.

The generative model refers to a model for determining a target creep value. In some embodiments, the generative model may be a function that determines a target creep value.

In some embodiments, the processor may call up a pre-stored generative model in the memory.

In 140, determine a target creep value based on the eigenvalue of the at least one field-of-view image by the generative model.

The target creep value refers to a creep value for the at least one field of view. The creep value refers to a value that reflects a creep stage. In some embodiments, the processor may determine a candidate creep value based on the eigenvalue of the field-of-view image by the generative model.

In some embodiments, the temperature of the furnace tube is 1100° C., the processor may process the field-of-view area of the at least one field-of-view image and the first area of the at least one field-of-view image based on the generative model to determine the first area fraction of the at least one field-of-view image; process the field-of-view area of the at least one field-of-view image and the second area of the at least one field-of-view image based on the generative model to determine the second area fraction of the at least one field-of-view image; and process the first area fraction of the at least one field-of-view image, the second area fraction of the at least one field-of-view image, and the aspect ratio of the at least one field-of-view image based on the generative model to determine the target creep value.

The generative model refers to a model used to determine the target creep value for a furnace tube at a temperature of 1100° C. In some embodiments, the generative model may be realized based on a formula (1), a formula (2), and a formula (3).

In some embodiments, the processor may determine the first area fraction by the formula (1):

$$A = S_1/S_0 \times 100\% \tag{1}$$

Where $S_0$ is the field-of-view area, $S_1$ is the first area, and A is the first area fraction with a unit of 1.

In some embodiments, the processor may determine the second area fraction by the formula (2):

$$B = S_2/S_0 \times 100\% \tag{2}$$

Where $S_0$ is the field-of-view area, $S_2$ is the second area, and B is the second area fraction with a unit of 1.

In some embodiments, the processor may determine a target creep value by the formula (3):

$$\bar{f} = [(\bar{a}\bar{A} + \bar{b}\bar{B} + \bar{c}\bar{C})/100] \times 100\% \tag{3}$$

Where $\bar{f}$ is the target creep value, $\bar{A}$ is an average of the first area fraction of the at least one field-of-view image, $\bar{B}$ is an average of the second area fraction of the at least one field-of-view image, $\bar{C}$ is an average of the aspect ratio of the at least one field-of-view image, $\bar{a}$, $\bar{b}$, and $\bar{c}$ are the weights of a weighted sum of $\bar{A}$, $\bar{B}$, and $\bar{C}$, where $\bar{a}$ is 1200, $\bar{b}$ is −10, and $\bar{c}$ is −0.3.

In some embodiments of the present disclosure, when the temperature of the furnace tube is 1100° C., the target creep value is determined through processing the field-of-view area, the first area fraction, the second area fraction, and an aspect ratio of the at least one field-of-view image based on the generative model, which fully considers the relationship between the creep stage and the area of the $M_{23}C_6$-type carbide and the $Ni_3Al$ phase of the peripheral lumpy precipitate in the austenitic grain boundary precipitate of the furnace tube material, or the area of the $M_7C_3$-type carbide of the internal thin strip-like precipitate in the austenitic grain boundary precipitate of the furnace tube material, or the aspect ratio of the $M_7C_3$-type carbide of the internal thin strip-like precipitate in the austenitic grain boundary precipitate of the furnace tube material, and is conducive to improving the accuracy of the generative model for determining the target creep value, thereby improving the reliability and accuracy of the creep stage.

In some embodiments, for a field-of-view image, the processor may determine, based on the eigenvalue of the field-of-view image, using the generative model, a candidate creep value of the field-of-view image; and determine the target creep value based on the candidate creep value of the at least one field-of-view image.

The candidate creep value refers to a creep value corresponding to each field of view.

In some embodiments, the generative model may be realized based on the formula (1), the formula (2), and a formula (4). In some embodiments, the temperature of the furnace tube is 1100° C., for a field-of-view image, the processor may determine a first area fraction and a second area fraction based on the formula (1) and the formula (2), and then determine the candidate creep value by the formula (4):

$$f = [(aA + bB + cC)/100] \times 100\% \tag{4}$$

Where f is the candidate creep value, A is the first area fraction of the above field-of-view image, B is the second area fraction of the above field-of-view image, C is the aspect ratio of the above field-of-view image, a, b, and c are weights of a weighted sum of A, B, and C, where a is 1200, b is −10, and c is −0.3.

In some embodiments, the target creep value is an arithmetic mean of the candidate creep value of the at least one field-of-view image.

In some embodiments of the present disclosure, the candidate creep value of the at least one field-of-view image is determined by the generative model based on the eigenvalue of the at least one field-of-view image, to further determine the target creep value, which is conducive to reducing the error caused by the single field-of-view image and improving the accuracy of determining the target creep value.

In 150, determine a creep stage based on the target creep value.

The creep stage refers to a stage of the ongoing deformation of the 27Cr44Ni5W3Al+microalloyed furnace tube. In some embodiments, the creep stage may include a creep first stage, an early phase of the creep second stage, a mid-phase of a creep second stage, an end phase of a creep second stage, and a creep third stage. More descriptions regarding each creep stage may be found in the preceding related description thereof.

The early phase of the creep second stage refers to a phase in which the alloy creep rate gradually stabilizes with the increase in creep time. The mid-phase of the creep second stage refers to a phase in which the alloy creep rate remains stable over a long period of time. The end phase of the creep second stage refers to a phase in which the alloy creep rate begins to have sight change at the end of the steady-state creep stage and the creep is about to enter the third stage.

In some embodiments, in response to the target creep value satisfying a first preset condition, the processor determines that the creep stage is a creep first stage; in response to the target creep value satisfying a second preset condition, determines that the creep stage is an early phase of the creep second stage; in response to the target creep value satisfying a third preset condition, determines that the creep stage is a mid-phase of the creep second stage; in response to the target creep value satisfying a fourth preset condition, determines that the creep stage is the end phase of the creep second stage; and in response to the target creep value satisfying a fifth preset condition, determines that the creep stage is the creep third stage, the target creep value that satisfies the first preset condition is less than the target creep value that satisfies the second preset condition, the target creep value that satisfies the second preset condition is less than the target creep value that satisfies the third preset condition, the target creep value that satisfies the third preset condition is less than the target creep value that satisfies the fourth preset condition, and the target creep value that satisfies the fourth preset condition is less than the target creep value that satisfies the fifth preset condition.

The first preset condition refers to a condition for determining whether the creep stage is a creep first stage. In some embodiments, the first preset condition may be that the target creep value is within a first preset range. For example, the first preset range may be a target creep value less than or equal to 10%.

The second preset condition refers to a condition for determining whether the creep stage is early phase of the creep second stage. In some embodiments, the second preset condition may be that the target creep value is within a second preset range. For example, the second preset range may be that the target creep value is greater than 10% and less than or equal to 30%.

The third preset condition refers to a condition for determining whether the creep stage is in the mid-phase of a creep second stage. In some embodiments, the third preset condition may be that the target creep value is within the third preset range. For example, the third preset range may be that the target creep value is greater than 30% and less than or equal to 70%.

The fourth preset condition refers to a condition for determining whether the creep stage is the end phase of a creep second stage. In some embodiments, the fourth preset condition may be that the target creep value is within the fourth preset range. For example, the fourth preset range may be that the target creep value is greater than 70% and less than or equal to 90%.

The fifth preset condition refers to a condition for determining whether the creep stage is the creep third stage. In some embodiments, the fifth preset condition may be that the target creep value is within the fifth preset range. For example, the fifth preset range may be that the target creep value is greater than 90%.

In some embodiments, the processor may predetermine the first preset range, the second preset range, the third preset range, the fourth preset range, and the fifth preset range based on default settings, or by a skilled person based on a priori experience.

Understandably, since the first preset range, the second preset range, the third preset range, the fourth preset range, and the fifth preset range are incremental and do not intersect, the target creep value that satisfies the first preset condition is less than the target creep value that satisfies the second preset condition, the target creep value that satisfies the second preset condition is less than the target creep value that satisfies the third preset condition, the target creep value that satisfies the third preset condition is less than the target creep value that satisfies the fourth preset condition, and the target creep value that satisfies the fourth preset condition is less than the target creep value that satisfies the fifth preset condition.

In some embodiments of the present disclosure, determining a creep stage based on a first preset condition, a second preset condition, a third preset condition, a fourth preset condition, and a fifth preset condition is conducive to quantifying the creep process of the material so as to more accurately and efficiently determine the creep stage of the material.

In 160, send the at least one field-of-view image and the creep stage to the display unit to cause the display unit to display the at least one field-of-view image and the creep stage.

In some embodiments, the processor may send the at least one field-of-view image and the creep stage to the display unit via a communication connection between the processor and the display unit.

In some embodiments, the display unit may display the received at least one field-of-view image and the creep stage on a display.

In some embodiments, the processor may generate a first marker information on at least one field-of-view image, the first marker information including a spatial marker, a contour marker, and a dimensional marker of a target precipitate, the target precipitate including an $M_7C_3$-type carbide, an $M_{23}C_6$-type carbide, a $Ni_3Al$ phase, etc.; and sending the first marker information to the display unit to cause the display unit to display the first marker information superimposed on the at least one field-of-view image.

The target precipitate refers to the precipitate to be recognized in the field-of-view image. In some embodiments, the target precipitate may include the $M_7C_3$-type carbide, the $M_{23}C_6$-type carbide, the $Ni_3Al$ phase, etc.

Figure 2:
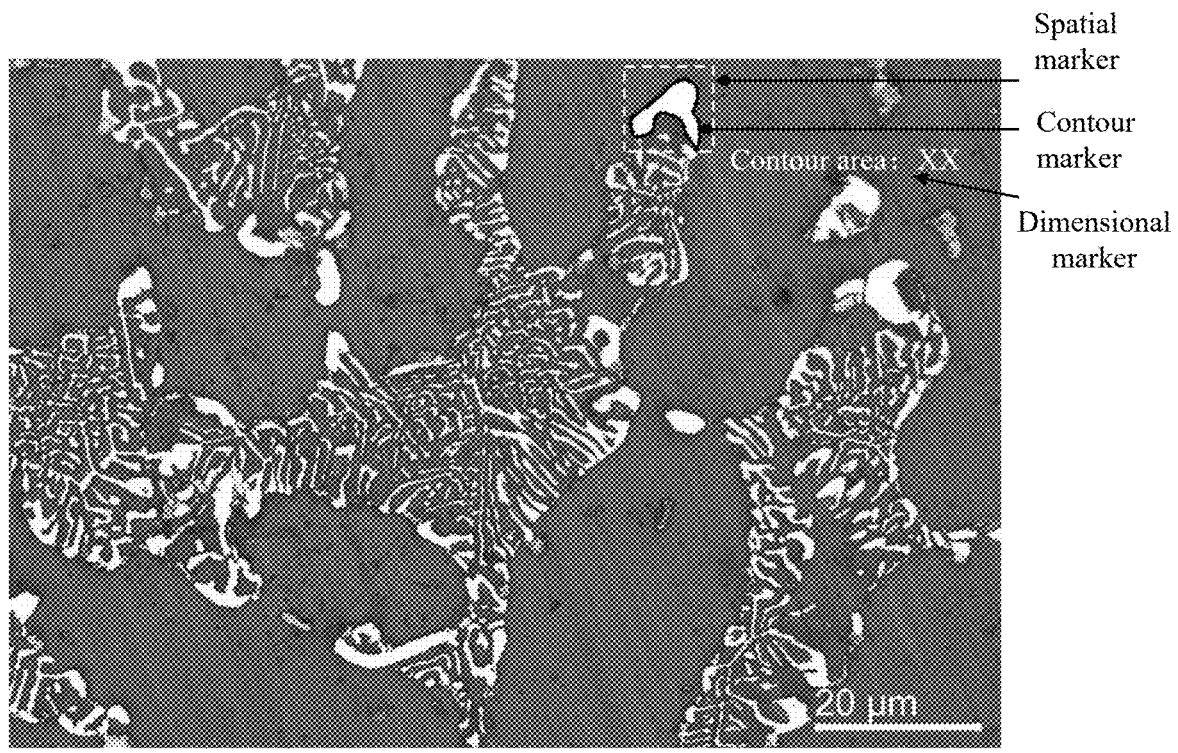
FIG. 2 is a schematic diagram illustrating the first marker information according to some embodiments of the present disclosure.

The first marker information refers to information that reflects the characteristics of the target precipitate. In some embodiments, the first marker information may include the spatial marker, the contour marker, and the dimensional marker, as shown in FIG. 2. In some embodiments, the processor may recognize, by a computer vision technique, the target precipitate in the field-of-view image, and thus obtain the first marker information.

The computer vision technique may include, but is not limited to, at least one of an image recognition algorithm, a machine learning model, or the like. The machine learning model for recognizing the target precipitate in the field-of-view images may be a Convolutional Neural Network (CNN), which may be obtained by training, and the training samples and training labels for training the machine learning model may be historical field-of-view images as well as manually labeled marker information. The training of the machine learning model may occur on a remote server, and the memory in the current creep stage determination system for aluminum-containing heat-resistant alloy furnace tube stores only the trained machine learning model. The remote server refers to a server that is not integrated with the creep stage determination system, and the remote server may be communicatively connected to the processor.

The spatial marker refers to a marker that embodies the position of the target precipitate in the field-of-view image. For example, the spatial marker may be a rectangle that is used to frame the location of the target precipitate in the field-of-view image. In some embodiments, the processor may use the smallest rectangle that can frame the target precipitate as the spatial marker.

The contour marker refers to a marker that embody the contour of the target precipitate. For example, the contour marker may be line segments that outlines the target precipitate in the field-of-view image. In some embodiments, the processor may take a contour consisting of a plurality of contour points as a contour marker, and the contour points refer to points on the target precipitate.

The dimensional marker refers to a marker that embody dimension of the target precipitate. For example, a dimensional marker may be an area of the contour of the target precipitate. In some embodiments, the processor may employ Image Pro® Plus 6.0 image analysis software to determine an area of contour of the target precipitate and use the area as a dimensional marker.

In some embodiments, the creep stage determination system for the aluminum-containing heat-resistant alloy furnace tube further includes an input unit. In some embodiments, the processor may, based on the input unit, obtain the first input marker of a user; generate the spatial marker based on the first input marker; determine the localized image based on the spatial marker; and determine the contour marker and the dimensional marker based on the localized image.

The input unit refers to a component that is used to enable interaction between the user and the processor. In some embodiments, the input unit may include a mobile device, tablet, laptop, or the like, or any combination thereof. In some embodiments, the input unit may be used to obtain a first input marker from the user.

The first input marker refers to a sub-region of the field-of-view image input by the user.

In some embodiments, the processor may obtain, via the input unit, the first input marker outlined by the user. For example, the processor may take a rectangular region that the user outlines with a mouse as the first input marker.

In some embodiments, the processor may identify a sub-region of the field-of-view image input by the user as the spatial marker. In some embodiments, the spatial marker may include one or more target precipitate. In some embodiments, the processor may remove the spatial marker without the target precipitate.

The localized image refers to a part of a field-of-view image. For example, the user draws a rectangular region using the input unit, and a part of the image in the field-of-view image within the rectangular region is a localized image.

In some embodiments, the processor may identify a part of the image in the field-of-view image corresponding to the first input marker as a localized image.

In some embodiments, the processor may recognize the contour marker and the dimensional marker in the localized image through computer vision techniques. More on computer vision techniques may be found in the preceding related description. When the computer vision technique is a machine learning model, the training labels used to train the machine learning model are different from those described in the previous section, the training labels are the contour marker and the dimensional marker in the user-selected localized image, which are manually labeled again.

In some embodiments, the processor may, based on the input unit, acquire the second input marker of the user; generate the spatial marker and the contour marker based on the second input marker; determine a localized contour based on the spatial marker and the contour marker; and recognize the localized contour to determine the dimensional marker.

In some embodiments, the input unit may also be used to obtain a second input marker from the user.

The second input marker refers to a sub-region of the field-of-view image input by the user and a contour of the target precipitate.

In some embodiments, the processor may identify a sub-region of the field-of-view image in the second input marker inputted by the user as a spatial marker and the contour of the target precipitate in the second input marker as a contour marker. In some embodiments, the spatial marker may include one or more target precipitate corresponding to one or more contour marker. In some embodiments, the processor may remove the spatial marker without target precipitate.

The localized contour refers to a contour of each target precipitate within the spatial marker outlined by the user. It can be appreciated that a plurality of localized contours may be included in the contour marker.

In some embodiments, the processor may identify each contour corresponding to each target precipitate in the contour identification as a localized contour.

In some embodiments, the processor may determine, via computer vision techniques, an area for each localized contour, thereby identifying each area as the dimensional marker. More on computer vision techniques may be found in the preceding related description. When the computer vision technique is a machine learning model, the training labels used to train the machine learning model are different from those in the previous section, and the training labels are the dimensional markers in the localized contour selected by the user that are again manually labeled.

In some embodiments of the present disclosure, determining a spatial marker, a contour marker, and a dimensional marker based on the first input marker or the second input marker can help to achieve customization of the display and improve user satisfaction.

In some embodiments, the display unit may display the first marker information superimposed on the at least one field-of-view image. For example, the field-of-view image may be on the bottom layer of the multi-layer image, and the first information marker may be displayed superimposed on an upper layer of the field-of-view image in a different color and/or line pattern.

In some embodiments of the present disclosure, generating the first marker information and displaying it superimposed on the display unit is conducive to clarifying a plurality of markers on the target precipitates, thereby facilitating a user to obtain information on the target precipitates in the field-of-view image, and improving the information acquisition efficiency.

In some embodiments of the present disclosure, determining an eigenvalue of afield-of-view image based on the field-of-view image and determining a candidate creep value of the field-of-view image based on the generative model and further determining a target creep value, and determining a creep stage based on the target creep value are beneficial for more intuitive and accurate prediction of the service life of the material to improve safety and reliability.

It should be noted that the foregoing description of process 100 is intended to be exemplary and illustrative only and does not limit the scope of application of the present disclosure. For a person skilled in the art, various corrections and changes may be made to process 100 under the guidance of the present disclosure. However, these corrections and changes remain within the scope of the present disclosure.

In some embodiments of the present disclosure, the processor may determine, based on the creep stage, a recommended overhaul time; and send the recommended overhaul time to the display unit to cause the display unit to display the recommended overhaul time.

The recommended overhaul time refers to a period of time between the current moment and the next moment of overhauling the furnace tube.

In some embodiments, the processor may determine a recommended overhaul time based on the creep stage by querying a first preset table. The first preset table may include the creep stage, the recommended overhaul time, and a relationship between the creep stage and the recommended overhaul time. In some embodiments, the technician may construct the first preset table based on knowledge experience. In some embodiments, the processor may organize historical data, such as a plurality of historical creep stages and historical recommended overhaul times, into a first preset table, and based on the first preset table, determine a recommended overhaul time. For example, the processor may count a large amount of historical failure data and determine the creep stage with the highest number of actual failures in the historical failure data as a high-risk stage; and then determine, based on the difference between the remaining creep stages and the high-risk stage, the recommended overhaul time; the smaller the difference, the shorter the recommended overhaul time. For example, the processor defines a numerical value for each processing stage, wherein the creep first stage is 1, the early phase of the creep second stage is 2, the mid-phase of a creep second stage is 3, the end phase of a creep second stage is 4, and the creep third stage is 5; based on the historical data, the processor statistically determines that the end phase of a creep second stage is a high-risk stage, and the current creep stage is the creep first stage, then the difference may be 3 (i.e., 4−1=3); the processor may determine the recommended overhaul time corresponding to the difference 3 by querying the fourth preset table constructed by the difference and the recommended overhaul time.

In some embodiments, the first preset table may be stored in the memory. When it is required to determine a recommended overhaul time, the processor may call up the first preset table.

In some embodiments, the processor may also determine a recommended overhaul time based on the creep stage and the creep dispersion.

The creep dispersion refers to the degree of dispersion of the candidate creep values. Understandably, the creep dispersion reflects the degree of homogeneity of the creep characteristics at various places of the furnace tube, which has reference significance for the formulation of the overhaul strategy.

In some embodiments, the processor may generate, based on the candidate creep value of the at least one field-of-view image, a creep dispersion; and send the candidate creep value of the at least one field-of-view image and the creep dispersion, to the display unit to cause the display unit to display the candidate creep value of the at least one field-of-view image and the creep dispersion.

In some embodiments, the processor may determine the creep dispersion based on the candidate creep value of the at least one field-of-view image by determining a variance or standard deviation. For example, the processor may use the variance or standard deviation, as described above, as the creep dispersion.

In some embodiments, the processor may send the candidate creep value and the creep dispersion to the display unit via network communication.

In some embodiments, the processor may query a first preset table to obtain a candidate overhaul time based on the creep stage. The processor may determine a correction value based on the creep dispersion. In turn, the processor may determine the difference between the candidate overhaul time and the correction value as the recommended overhaul time. The greater the creep dispersion, the greater the correction value. In some embodiments, the processor may determine the correction value by querying a third preset table based on the creep dispersion. The third preset table may be manually predetermined based on priori experience.

In some embodiments of the present disclosure, checks should be performed earlier because the greater the creep dispersion, the more heterogeneous and uncertain the creep characteristics at various location of the furnace tube. Determining the recommended overhaul time based on the creep stage and the creep dispersion is conducive to improving the accuracy of the recommended overhaul time.

In some embodiments, the processor may send the recommended overhaul time to the display unit via a network communication connection to cause the display unit to display the recommended overhaul time for the user's reference.

In some embodiments of the present disclosure, a recommended overhaul time is determined based on the creep stage and sent to the display unit, which facilitates timely overhauling of the furnace tube.

Figure 3:
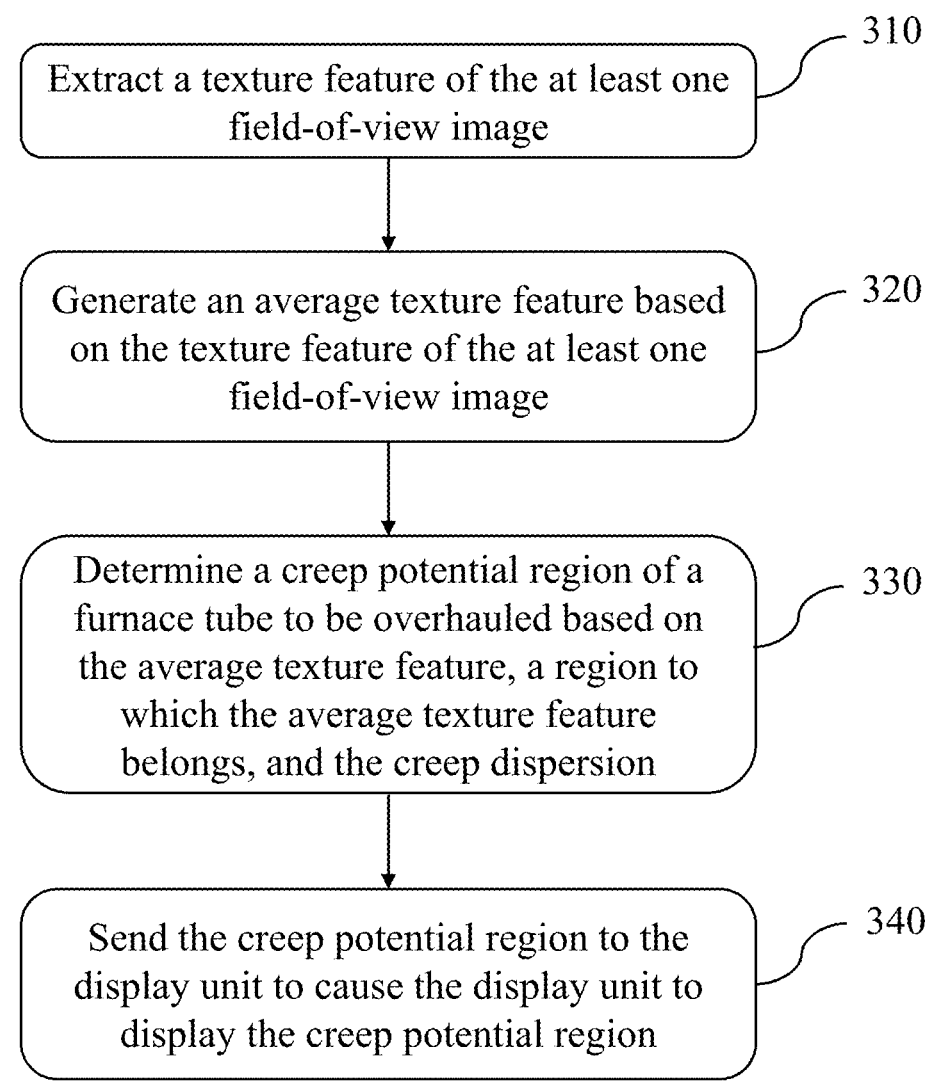
FIG. 3 is a flowchart illustrating a process of determining a creep potential region according to some embodiments of the present disclosure.

FIG. 3 is a flowchart illustrating a process for determining a creep potential region according to some embodiments of the present disclosure. As shown in FIG. 3, a process 300 includes operations 310-340 as described below. In some embodiments, the process 300 may be executed by a processor.

In some embodiments, the processor may extract a texture feature of the at least one field-of-view image; generate an average texture feature based on the texture feature of the at least one field-of-view image; based on the average texture feature, a region to which the average texture feature belongs, and a creep dispersion determine a creep potential region of a furnace tube to be overhauled; and send the creep potential region to a display unit to cause the display unit to display the creep potential region.

In 310, extract a texture feature of the at least one field-of-view image.

The texture feature refers to statistical or geometric feature that describes the surface structure or pattern in different regions of the field-of-view image. In some embodiments, the texture feature may be in the form of text, an image, or the like.

In some embodiments, the processor may obtain the texture feature through computer vision techniques (e.g., recognition based on a trained convolutional neural network).

In 320, generate an average texture feature based on the texture feature of the at least one field-of-view image.

The average texture feature refers to an average of a plurality of field-of-view image texture features. In some embodiments, the average may be an arithmetic mean or a weighted average. In some embodiments, when the texture feature is in the form of text, the texture features in the form of text may be first quantized into numbers (e.g., quantized by predetermined rules based on the type, density, etc. of the texture), and then an average of the quantized numbers may be computed, and then finally, the obtained average may be reverse-matched by the aforementioned predetermined rules to obtain an average texture feature.

In some embodiments, the processor may determine an average or a weighted average based on the texture features of the plurality of field-of-view images, determining the determined average or weighted average as the texture feature.

In 330, determine a creep potential region of a furnace tube to be overhauled based on the average texture feature, a region to which the average texture feature belongs, and the creep dispersion. More descriptions regarding the creep dispersion may be found in the FIG. 2 related description thereof, The region to which the average texture feature belongs refers to the region where the texture features and the average texture feature are located.

In some embodiments, the processor may divide the furnace tube into the following regions: a region A (0-1/8 wall thickness region), a region B (1/8-2/8 wall thickness region), a region C (2/8-3/8 wall thickness region), . . . . The processor may determine the region in which the specimen is, the specimen being used to determine the average texture feature, as the region to which the average texture feature belong. If the specimen is obtained from the region A, and an average texture feature is determined for the specimen, then the region to which that average texture feature belongs is referred to as the region A.

The furnace tube to be overhauled refers to the furnace tube waiting to be overhauled.

The creep potential region refers to the region in the furnace tube where the hazard exists.

In some embodiments, the processor may determine a creep potential region of the furnace tube to be overhauled by querying the second preset table based on the average texture feature, the region to which the average texture feature belongs, and the creep dispersion. In some embodiments, the technician may construct the second preset table based on knowledge and experience. In some embodiments, the processor may organize historical data such as a plurality of historical average texture features, the region to which the historical average texture feature belongs, a historical creep dispersion, and a historical creep potential region into a second preset table, and based on the second preset table, determine the creep potential region. For example, for each historical failure data in the large amount of historical failure data, the processor takes the average texture feature, the region to which the average texture feature belongs, and the creep dispersion of the specimen on which the microscopic inspection was actually performed in the historical failure data as the historical average texture feature, the region to which the historical average texture feature belongs, and the historical creep dispersion, and takes the region for which the abnormality actually exists in the historical failure data as the historical creep potential region, thereby constructing a second preset table.

In some embodiments, the second preset table may be stored in the memory. When it is necessary to determine the creep potential region, the processor may call up the second preset table.

In 340, send the creep potential region to the display unit to cause the display unit to display the creep potential region.

Exemplarily, when the furnace tube is divided into a region A (0-1/8 wall thickness region), a region B (1/8-2/8 wall thickness region), a region C (2/8-3/8 wall thickness region), . . . , the processor samples the region A to obtain a specimen, and determines the average texture feature, the region to which the average texture feature belongs, and the creep dispersion of the specimen. Then, the processor determines the creep potential region as the region B based on the average texture feature, the region to which the average texture feature belongs, and the creep dispersion of the specimen via the second preset table. The processor sends the creep potential region to the display unit to cause the display unit to display the creep potential region. Thus, the user may be reminded to take another sample from the region B for microscopic observation.

In some embodiments of the present disclosure, determining a creep potential region based on the average texture feature, the region to which the average texture feature belongs, and the creep dispersion is conducive to timely detecting the creep potential region, thus making a more accurate sampling judgment.

Figure 4:
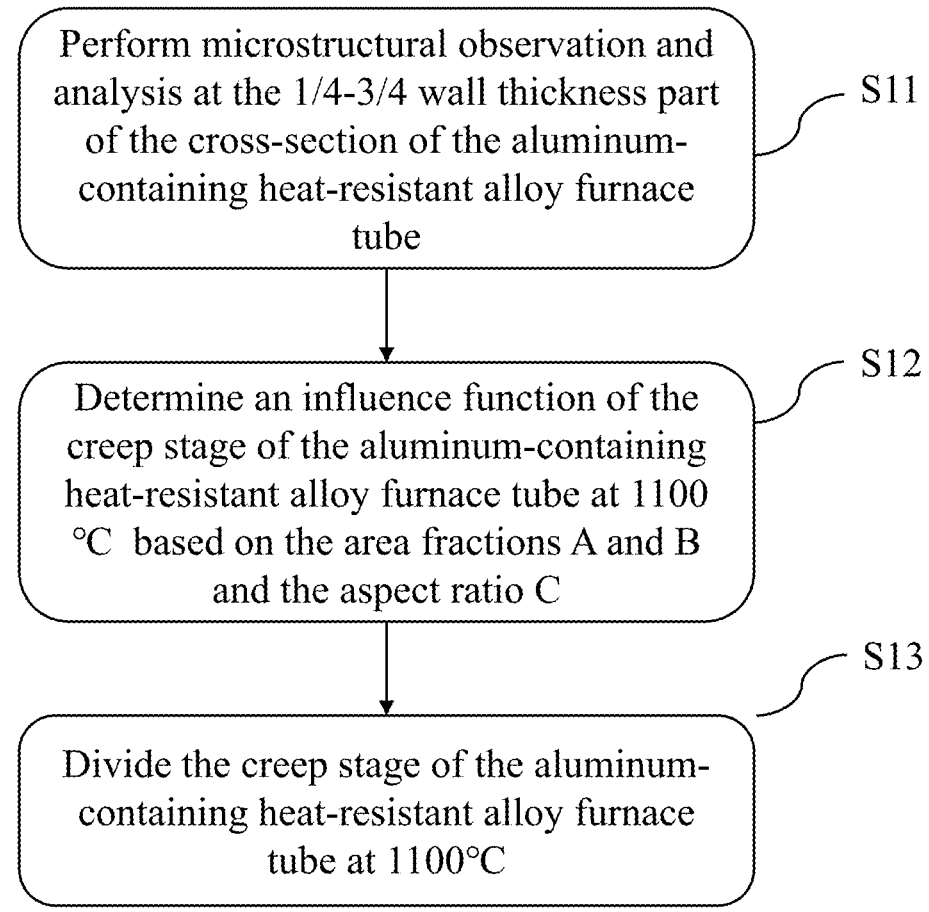
FIG. 4 is a flowchart illustrating a method for determining a creep stage according to some embodiments of the present disclosure.

FIG. 4 is a flowchart illustrating a method for determining a creep stage according to some embodiments of the present disclosure. As shown in FIG. 4, the process includes operations S11-S13 as described below. In some embodiments, the process may be executed by a processor.

In some embodiments, a method of determining a creep stage of an aluminum-containing heat-resistant alloy furnace tube at a temperature of 1100° C. includes the following operations.

In S11, perform microstructural observation and analysis at the 1/4-3/4 wall thickness part of the cross-section of the aluminum-containing heat-resistant alloy furnace tube.

In some embodiments, the processor measures an area $S_1$ of the peripheral lumpy precipitate $M_{23}C_6$-type carbide and a $Ni_3Al$ phase in the austenitic grain boundary precipitate of the furnace tube material within a field-of-view area $S_0$, determines an area fraction of the area $S_1$ of the peripheral lumpy precipitate $M_{23}C_6$-type carbide and a $Ni_3Al$ phase in the austenitic grain boundary precipitate to the field-of-view area $S_0$ as $A=S_1/S_0\times 100\%$, with a unit of 1; measures an area $S_2$ of the internal thin strip-like precipitate $M_7C_3$-type carbide in the austenitic grain boundary precipitate of the furnace tube material within the field-of-view area $S_0$, determines an area fraction of the area $S_2$ of the internal thin strip-like precipitate $M_7C_3$-type carbide in the austenitic grain boundary precipitate to the field-of-view area $S_0$ as $B=S_2/S_0\times100\%$, with a unit of 1; and measures the aspect ratio C of the internal thin strip-like precipitate $M_7C_3$-type carbide in the austenitic grain boundary precipitate of the furnace tube material within the field-of-view area $S_0$, with a unit of 1.

In S12, determine an influence function of the creep stage of the aluminum-containing heat-resistant alloy furnace tube at 1100° C. based on the area fractions A and B and the aspect ratio C.

$f(A,B,C)=[(aA+bB+cC)/100]\times100\%$, where $a$ is 1200, $b$ is −10, and $c$ is −0.3.

In S13, divide the creep stage of the aluminum-containing heat-resistant alloy furnace tube at 1100° C.

If $f(A,B,C)\leq10\%$, a creep state of 27Cr44Ni5W3Al+ microalloyed furnace tube is determined as the creep first stage; if $10\%<f(A,B,C)\leq30\%$, the creep state of 27Cr44Ni5W3Al+microalloyed furnace tube is determined as the early phase of the creep second stage; if $30\%<f(A,B,C)\leq70\%$, the creep state of 27Cr44Ni5W3Al+microalloyed furnace tube is determined as the mid-phase of the creep second stage; if $70\%<f(A,B,C)\leq90\%$, the creep state of 27Cr44Ni5W3Al+microalloyed furnace tube is determined as the end phase of the creep second stage; if $90\%<f(A,B,C)$, the creep state of 27Cr44Ni5W3Al+microalloyed furnace tube is determined as the creep third stage.

In some embodiments, the processor employs an Olympus® GX53 metallurgical microscope for microstructure observation with a magnification of 1,000 times, and no fewer than 20 fields of view are randomly selected for each specimen for microstructure observation.

In some embodiments, the processor performs microstructure analysis of the microstructure photographs using Image Pro® Plus 6.0 image analysis software, with the measurements being an arithmetic mean of all fields of view measurements.

In some embodiments, the processor analyzes the microstructure photographs using Image Pro® Plus 6.0 image analysis software, and the regions are selected with a range of 10, a thresh of 3, a smooth of 1, and a speed of 2.

In some embodiments, the austenite grain boundary and intragranular total precipitate of the furnace tube material include the $M_{23}C_6$-type carbide, the $M_7C_3$-type carbide, and the $Ni_3Al$ phase.

In some embodiments, the aluminum-containing heat-resistant alloy furnace tube is a 27Cr44Ni5W3Al+microalloyed furnace tube.

It should be noted that the area $S_1$ of the peripheral lumpy precipitate $M_{23}C_6$-type carbide and the $Ni_3Al$ phase in the austenitic grain boundary precipitate of the furnace tube material may be referred to as the first area; the area $S_2$ of the internal thin strip-like precipitate $M_7C_3$-type carbide in the austenitic grain boundary precipitate of the furnace tube material may be referred to as the second area; the area fraction of the area $S_1$ of the peripheral lumpy precipitate $M_{23}C_6$-type carbide and the $Ni_3Al$ phase in the austenitic grain boundary precipitate to the field-of-view area $S_0$ may be referred to as the first area fraction; the area fraction of the area $S_2$ of the internal thin strip-like precipitate $M_7C_3$-type carbide in the austenitic grain boundary precipitate to the field-of-view area $S_0$ may be referred to as the second area fraction; and the influence function may be referred to as the target creep value.

More descriptions regarding operations S11-S13 may be found in FIG. 1 and its related description thereof.

It should be noted that the foregoing description of the process is for the purpose of exemplification and illustration only and does not limit the scope of application of the present disclosure. For a person skilled in the art, various corrections and changes to the process may be made under the guidance of the present disclosure. However, these corrections and changes remain within the scope of the present disclosure.

The method of determining the creep stage of the aluminum-containing heat-resistant alloy furnace tube will be described in detail below by Examples 1-4. It should be noted that the temperature and microstructure observation position in Examples 1-4 are only for the purpose of illustrating the method of determining the creep stage of the aluminum-containing heat-resistant alloy furnace tube, and do not limit the scope of protection of the present disclosure.

Example 1

Figure 7:
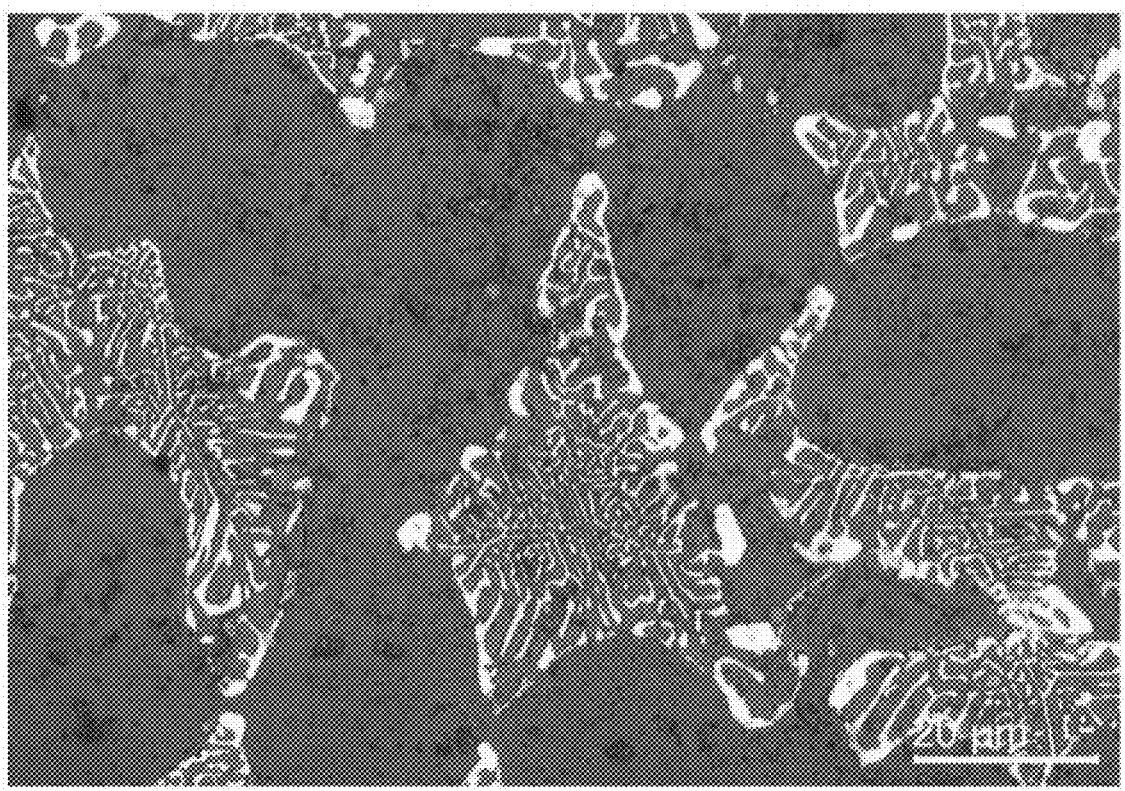
FIG. 7 is a microstructure photograph illustrating 1#27Cr44Ni5W3Al+microalloyed furnace tube of Example 1 according to some embodiments of the present disclosure.

The present embodiment provides a creep stage determination method for an aluminum-containing heat-resistant alloy furnace tube at a temperature of 1100° C., specifically comprising the following operations:

S1, the 27Cr44Ni5W3Al+microalloyed furnace tube sample subjected to creep test at 1100° C. and 17 MPa for 10 h was selected, which was recorded as 1#27Cr44Ni5W3Al+microalloyed furnace tube sample, the Olympus® GX53 metallurgical microscope was used for performing microstructure observation at the 1/2 wall thickness part of the cross-section of the 1#27Cr44Ni5W3Al+ microalloyed furnace tube sample, with the magnification of 1000 times, and the typical microstructure photograph was shown in FIG. 7.

S2, Image Pro® Plus 6.0 image analysis software was used to analyze the microstructure photograph, and the region was selected with a range of 10, a thresh of 3, a smooth of 1, and a speed of 2.

For the first field of view, the measured area of the peripheral lumpy precipitate $M_{23}C_6$-type carbide and the $Ni_3Al$ phase in the austenitic grain boundary precipitate of the furnace tube material within the field-of-view area $S_0$ was also referred to as the first area $S_1$, and the determined area fraction of the area $S_1$ of the peripheral lumpy precipitate $M_{23}C_6$-type carbide and the $Ni_3Al$ phase in the austenitic grain boundary precipitate to the field-of-view area $S_0$ was also referred to as the first area fraction $A=S_1/S_0\times100\%$, with a unit of 1.

The measured area of the internal thin strip-like precipitate $M_7C_3$-type carbide in the austenitic grain boundary precipitate of the furnace tube material within field-of-view area $S_0$ was also referred to as the second area $S_2$, and the determined area fraction of the area $S_2$ of the internal thin strip-like precipitate $M_7C_3$-type carbide in the austenitic grain boundary precipitate to the field-of-view area $S_0$ was also referred to as the second area fraction $B=S_2/S_0\times100\%$, with a unit of 1.

The aspect ratio C, with a unit of 1, of the internal thin strip-like precipitate $M_7C_3$ in the austenitic grain boundary precipitate of the furnace tube material within the field-of-view area $S_0$ was measured.

The microstructure observation interface was switched, and then 19 fields of view were randomly selected. It was determined that the average $\overline{A}$ of the first area fraction of the 1#27Cr44Ni5W3Al+microalloyed furnace tube sample during 20 tests was 1.1%, the average $\overline{B}$ of the second area fraction of the 1#27Cr44Ni5W3Al+microalloyed furnace tube sample during 20 tests was 3.3%, and the average $\overline{C}$ of the aspect ratio of 1#27Cr44Ni5W3Al+microalloyed furnace tube sample during 20 tests was 9.8.

S3, based on the percentage of time of the different stages of creep, 0% t was defined when creep has not yet begun, and 100% t was defined at the end of the creep third stage; and the target creep value of the creep stage of the 1#27Cr44Ni5W3Al+microalloyed furnace tube sample at 1100° C. was determined as: $\bar{f}=[(a\bar{A}+b\bar{B}+c\bar{C})/100]\times100\%=[(1200\times0.011-10\times0.033-0.3\times9.8)/100]\times100\%=10\%$.

S4, f(A,B,C)≤10%, and the creep state of the 1#27Cr44Ni5W3Al+microalloyed furnace tube sample was determined as the creep first stage.

Verification Test

A new furnace tube with the same material, same specification, same batch as the 1#27Cr44Ni5W3Al+microalloyed furnace tube sample and not in service was selected for carrying out a high-temperature creep test at 1100° C. and 17 MPa, the creep time-strain rate curve was shown in FIG. 6, the total creep test time was $t_0$, the time of the creep first stage, the creep second stage, and the creep third stage time were $t_1$, $t_2$, and $t_3$, respectively, and $t_0=t_1+t_2+t_3$. The total creep rupture time of the test was 154 h, and the time of the creep first stage, the creep second stage, and the creep third stage were 15 h, 122 h, and 17 h, respectively.

A sample subjected to creep test at 1100° C. and 17 MPa for 10 h, which was the same as the 1#27Cr44Ni5W3Al+microalloyed furnace tube sample, was selected for carrying out high-temperature creep test at 1100° C. and 17 MPa, and the total creep rupture time of the test was 140 h.

Compared with the new furnace tube not in service, at 1100° C. and 17 MPa, the creep fracture time loss of the 1#27Cr44Ni5W3Al+microalloyed furnace tube sample was 14 h, accounting for about 9% of the total creep life of the new furnace tube not in service, and the creep state of the 1#27Cr44Ni5W3Al+microalloyed furnace tube sample was determined as the creep first stage. The determination result was consistent with the calculation result (10%) of the target creep value.

Example 2

Figure 8:
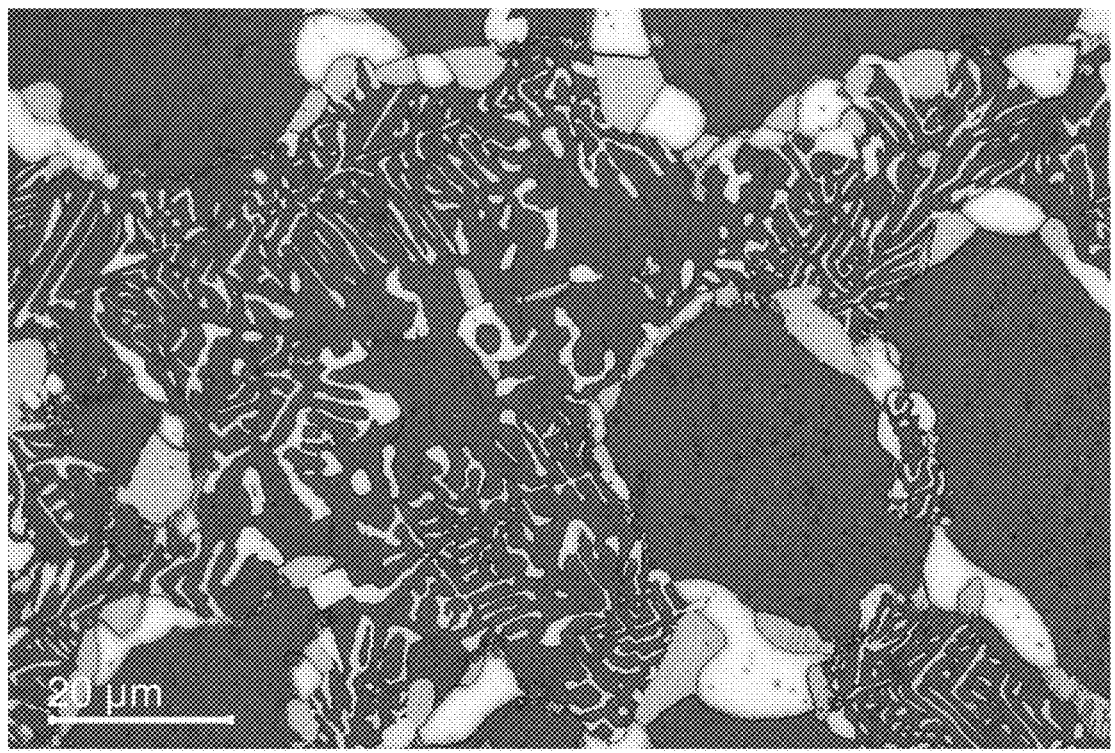
FIG. 8 is a microstructure photograph illustrating 2#27Cr44Ni5W3Al+microalloyed furnace tube of Example 2 according to some embodiments of the present disclosure.

The present embodiment provides a creep stage determination method for an aluminum-containing heat-resistant alloy furnace tube at a temperature of 1100° C., specifically comprising the following operations:

S1, the 27Cr44Ni5W3Al+microalloyed furnace tube sample with the highest wall temperature of 1100° C. during service was selected, which was recorded as 2#27Cr44Ni5W3Al+microalloyed furnace tube sample, the Olympus® GX53 metallurgical microscope was used for performing microstructure observation at the 1/2 wall thickness part of the cross-section of the 2#27Cr44Ni5W3Al+microalloyed furnace tube sample, with the magnification of 1000 times, and the typical microstructure photograph was shown in FIG. 8.

S2, Image Pro® Plus 6.0 image analysis software was used to analyze the microstructure photograph, and the region was selected with a range of 10, a thresh of 3, a smooth of 1, and a speed of 2.

For the first field of view, the area $S_1$ of the peripheral lumpy precipitate $M_{23}C_6$-type carbide and the $Ni_3Al$ phase in the austenitic grain boundary precipitate of the furnace tube material within the field-of-view area $S_0$ was measured and the first area fraction of the area $S_1$ of the peripheral lumpy precipitate $M_{23}C_6$-type carbide and the $Ni_3Al$ phase in the austenitic grain boundary precipitate to the field-of-view area $S_0$ was determined as the first area fraction $A=S_1/S_0\times100\%$, with a unit of 1.

The area $S_2$ of the internal thin strip-like precipitate $M_7C_3$-type carbide in the austenitic grain boundary precipitate of the furnace tube material within the field-of-view area $S_0$ was measured, and the second area fraction of the area $S_2$ of the internal thin strip-like precipitate $M_7C_3$-type carbide in the austenitic grain boundary precipitate to the field-of-view area $S_0$ was determined as the second area fraction $B=S_2/S_0\times100\%$, with a unit of 1.

The aspect ratio, with a unit of 1, of the internal thin strip-like precipitate $M_7C_3$-type carbide in the austenitic grain boundary precipitate of the furnace tube material within the field-of-view area $S_0$ was measured.

The microstructure observation interface was switched, and then 19 fields of view were randomly selected. It was determined that the average $\bar{A}$ of the first area fraction of the 2#27Cr44Ni5W3Al+microalloyed furnace tube sample during 20 tests was 5.9%, the average $\bar{B}$ of the second area fraction of the 2#27Cr44Ni5W3Al+microalloyed furnace tube sample during 20 tests was 3.0%, and the average $\bar{C}$ of the aspect ratio of 2#27Cr44Ni5W3Al+microalloyed furnace tube sample during 20 tests was 7.4.

S3, based on the percentage of time of the different stages of creep, 0% t was defined when creep has not yet begun, and 100% t was defined at the end of the creep third stage; and the target creep value of the creep stage of the 2#27Cr44Ni5W3Al+microalloyed furnace tube sample at 1100° C. was determined as: $\bar{f}=[(a\bar{A}+b\bar{B}+c\bar{C})/100]\times100\%=[(1200\times0.059-10\times0.030-0.3\times7.4)/100]\times100\%=68\%$.

S4, 30%<f(A,B,C)≤70%, and the creep state of the 2#27Cr44Ni5W3Al+microalloyed furnace tube sample was determined as the mid-phase of the creep second stage.

Verification Test

A new furnace tube with the same material, same specification, same batch as the 2#27Cr44Ni5W3Al+microalloyed furnace tube sample and not in service was selected for carrying out a high-temperature creep test at 1100° C. and 17 MPa, the creep time-strain rate curve was shown in FIG. 6, the total creep test time was $t_0$, the time of the creep first stage, the creep second stage, and the creep third stage time were $t_1$, $t_2$, and $t_3$, respectively, and $t_0=t_1+t_2+t_3$. The total creep rupture time of the test was 154 h, and the time of the creep first stage, the creep second stage, and the creep third stage were 15 h, 122 h, and 17 h, respectively.

The 2#27Cr44Ni5W3Al+microalloyed furnace tube sample was selected for carrying out high-temperature creep test at 1100° C. and 17 MPa, and the total creep rupture time of the test was 47 h.

Compared with the new furnace tube not in service, the creep fracture time loss of the 2#27Cr44Ni5W3Al+microalloyed furnace tube sample was 107 h, accounting for about 69% of the total creep life of the new furnace tube not in service, and the creep state of the 2#27Cr44Ni5W3Al+microalloyed furnace tube sample was determined as the mid-phase of the creep second stage. The determination result was consistent with the calculation result (68%) of the target creep value.

Example 3

Figure 9:
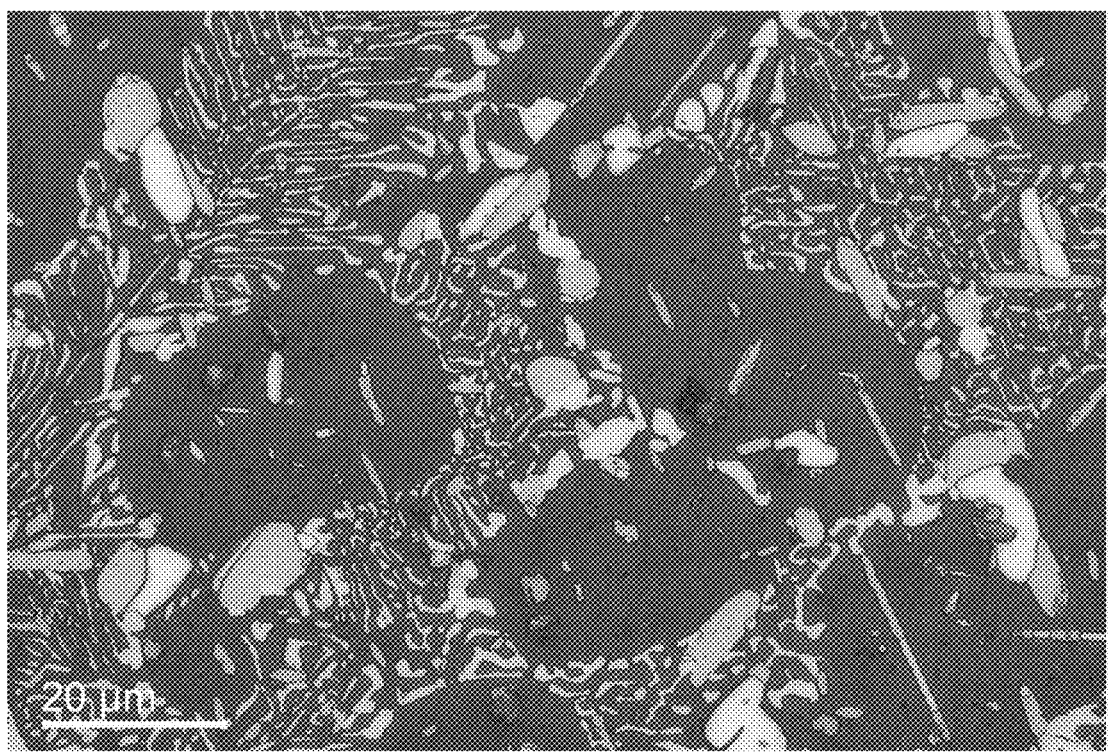
FIG. 9 is a microstructure photograph illustrating 3#27Cr44Ni5W3Al+microalloyed furnace tube of Example 3 according to some embodiments of the present disclosure.

The present embodiment provides a creep stage determination method for an aluminum-containing heat-resistant alloy furnace tube at a temperature of 1100° C., specifically comprising the following operations:

S1, the 27Cr44Ni5W3Al+microalloyed furnace tube sample with the highest wall temperature of 1100° C. during service was selected, which was recorded as the 3#27Cr44Ni5W3Al+microalloyed furnace tube sample, the Olympus® GX53 metallurgical microscope was used for performing microstructure observation at the 1/2 wall thickness part of the cross-section of the 3#27Cr44Ni5W3Al+microalloyed furnace tube sample, with the magnification of 1000 times, and the typical microstructure photograph was shown in FIG. 9.

S2, Image Pro® Plus 6.0 image analysis software was used to analyze the microstructure photograph, and the region was selected with a range of 10, a thresh of 3, a smooth of 1, and a speed of 2.

For the first field of view, the area $S_1$ of the peripheral lumpy precipitate $M_{23}C_6$-type carbide and the $Ni_3Al$ phase in the austenitic grain boundary precipitate of the furnace tube material within the field-of-view area $S_0$ was measured, and the area fraction of the area $S_1$ of the peripheral lumpy precipitate $M_{23}C_6$-type carbide and the $Ni_3Al$ phase in the austenitic grain boundary precipitate to the field-of-view area $S_0$ was determined as the first area fraction $A=S_1/S_0\times 100\%$, with a unit of 1.

The area $S_2$ of the internal thin strip-like precipitate $M_7C_3$-type carbide in the austenitic grain boundary precipitate of the furnace tube material within the field-of-view area $S_0$ was measured, and the area fraction of the area $S_2$ of the internal thin strip-like precipitate $M_7C_3$-type carbide in the austenitic grain boundary precipitate to the field-of-view area $S_0$ was determined as the second area fraction $B=S_2/S_0\times 100\%$, with a unit of 1.

The aspect ratio of the internal thin strip-like precipitate $M_7C_3$-type carbide in the austenitic grain boundary precipitate of the furnace tube material within the field-of-view area $S_0$ was measured.

The microstructure observation interface was switched, and then 19 fields of view were randomly selected. It was determined that the average $\overline{A}$ of the first area fraction of the 3#27Cr44Ni5W3Al+microalloyed furnace tube sample during 20 tests was 5.4%, the average $\overline{B}$ of the second area fraction $\overline{B}$ of the 3#27Cr44Ni5W3Al+microalloyed furnace tube sample during 20 tests was 3.1%, and the average $\overline{C}$ of the aspect ratio of 3#27Cr44Ni5W3Al+microalloyed furnace tube sample during 20 tests was 7.1.

S3, based on the percentage of time of the different stages of creep, 0% t was defined when creep has not yet begun, and 100% t was defined at the end of the creep third stage; and the target creep value of the creep stage of the 3#27Cr44Ni5W3Al+microalloyed furnace tube sample at 1100° C. was determined as: $\overline{f}=[(a\overline{A}+b\overline{B}+c\overline{C})/100]\times 100\%=[(1200\times 0.054-10\times 0.031-0.3\times 7.1)/100]\times 100\%=62\%$.

S4, $30\%<f(A,B,C)\leq 70\%$, and the creep state of the 3#27Cr44Ni5W3Al+microalloyed furnace tube sample was determined as the mid-phase of the creep second stage.

Verification Test

A new furnace tube with the same material, same specification, same batch as the 3#27Cr44Ni5W3Al+microalloyed furnace tube sample and not in service was selected for carrying out a high-temperature creep test at 1100° C. and 17 MPa, the creep time-strain rate curve was shown in FIG. 6, the total creep test time was $t_0$, the time of the creep first stage, the creep second stage, and the creep third stage time were $t_1$, $t_2$, and $t_3$, respectively, and $t_0=t_1+t_2+t_3$. The total creep rupture time of the test was 154 h, and the time of the creep first stage, the creep second stage, and the creep third stage were 15 h, 122 h, and 17 h, respectively.

The 3#27Cr44Ni5W3Al+microalloyed furnace tube sample was selected for carrying out high-temperature creep test at 1100° C. and 17 MPa, and the total creep rupture of the test was 55 h.

Compared with the new furnace tube not in service, the creep fracture time loss of the 3#27Cr44Ni5W3Al+microalloyed furnace tube sample was 99 h, accounting for about 64% of the total creep rupture time of the new furnace tube not in service, and the creep state of the 3#27Cr44Ni5W3Al+microalloyed furnace tube sample was determined as the mid-phase of the creep second stage. The determination result was consistent with the calculation result (62%) of the target creep value.

Example 4

Figure 10:
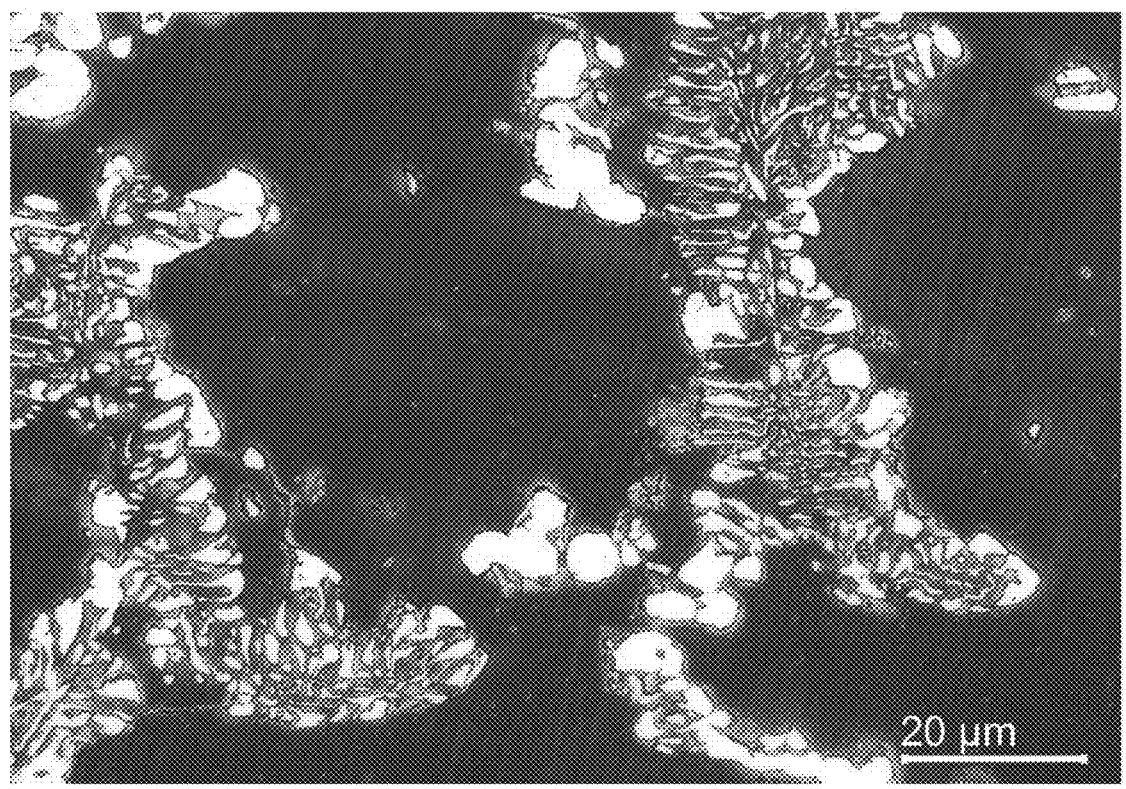
FIG. 10 is a microstructure photograph illustrating 4#27Cr44Ni5W3Al+microalloyed furnace tube of Example 4 according to some embodiments of the present disclosure.

The present embodiment provides a creep stage determination method for a 27Cr44Ni5W3Al+microalloyed furnace tube at a temperature of 1100° C., specifically comprising the following operations:

S1, the 27Cr44Ni5W3Al+microalloyed furnace tube sample subjected to creep test at 1100° C. and 17 MPa for 140 h was selected, which was recorded as 4#27Cr44Ni5W3Al+microalloyed furnace tube sample, the Olympus® GX53 metallurgical microscope was used for performing microstructure observation at the 1/2 wall thickness part of the cross-section of the 4#27Cr44Ni5W3Al+microalloyed furnace tube sample, with the magnification of 1000 times, and the typical microstructure photograph was shown in FIG. 10.

S2, Image Pro® Plus 6.0 image analysis software was used to analyze the microstructure photograph, and the region was selected with a range of 10, a thresh of 3, a smooth of 1, and a speed of 2.

For the first field of view, the measured area of the peripheral lumpy precipitate $M_{23}C_6$-type carbide and the $Ni_3Al$ phase in the austenitic grain boundary precipitate of the furnace tube material within the field-of-view area $S_0$ was also referred to as a first area $S_1$, and the area fraction of the area $S_1$ of the peripheral lumpy precipitate $M_{23}C_6$-type carbide and the $Ni_3Al$ phase in the austenitic grain boundary precipitate to the field-of-view area $S_0$ was also referred to as the first area fraction $A=S_1/S_0\times 100\%$, with a unit of 1.

The measured area of the internal thin strip-like precipitate $M_7C_3$-type carbide in the austenitic grain boundary precipitate of the furnace tube material within the field-of-view area $S_0$ was also referred to as the second area $S_2$, and the determined area fraction of the area $S_2$ of the internal thin strip-like precipitate $M_7C_3$-type carbide in the austenitic grain boundary precipitate to the field-of-view area $S_0$ was also referred to as the second area fraction $B=S_2/S_0\times 100\%$, with a unit of 1.

The aspect ratio C, with a unit of 1, of the internal thin strip-like precipitate $M_7C_3$-type carbide in the austenitic grain boundary precipitate of the furnace tube material within the field-of-view area $S_0$ was measured.

The microstructure observation interface was switched, and then 19 fields of view were randomly selected. It was determined that the average $\overline{A}$ of the first area fraction of the 4#27Cr44Ni5W3Al+microalloyed furnace tube sample during 20 tests was 7.7%, the average $\overline{B}$ of the second area fraction of the 4#27Cr44Ni5W3Al+microalloyed furnace tube sample during 20 tests was 2.1%, and the average $\overline{C}$ of the aspect ratio of the 4#27Cr44Ni5W3Al+microalloyed furnace tube sample during 20 tests was 3.9.

S3, based on the percentage of time of the different stages of creep, 0% t was defined when creep has not yet begun, and 100% t was defined at the end of the creep third stage; and the target creep value of the creep stage of the 4#27Cr44Ni5W3Al+microalloyed furnace tube sample at 1100° C. was determined as: $\bar{f}=[(a\bar{A}+b\bar{B}+c\bar{C})/100]\times100\%=[(1200\times0.077-10\times0.021-0.3\times3.9)/100]\times100\%=91\%$.

S4, f(A,B,C)>90%, and the creep state of the 4#27Cr44Ni5W3Al+microalloyed furnace tube sample was determined as the creep third stage.

Verification Test

A new furnace tube with the same material, same specification, same batch as the 4#27Cr44Ni5W3Al+microalloyed furnace tube sample and not in service was selected for carrying out a high-temperature creep test at 1100° C. and 17 MPa, the creep time-strain rate curve was shown in FIG. 6, the total creep test time was $t_0$, the time of the creep first stage, the creep second stage, and the creep third stage time were $t_1$, $t_2$, and $t_3$, respectively, and $t_0=t_1+t_2+t_3$. The total creep rupture time of the test was 154 h, and the time of the creep first stage, the creep second stage, and the creep third stage were 15 h, 122 h, and 17 h, respectively.

A sample subjected to creep test at 1100° C. and 17 MPa for 140 h, which was the same as the 4#27Cr44Ni5W3Al+microalloyed furnace tube sample, was selected for carrying out high-temperature creep test at 1100° C. and 17 MPa, and the total creep rupture time of the test was 12 h.

Compared with the new furnace tube not in service, the creep fracture time loss of the 4#27Cr44Ni5W3Al+microalloyed furnace tube sample was 142 h, accounting for about 92% of the total creep rupture time of the new furnace tube not in service, and the creep state of the 4#27Cr44Ni5W3Al+microalloyed furnace tube sample was determined as the creep third stage. The determination result was consistent with the calculation result (91%) of the target creep value.

One or more embodiments of the present disclosure provide a computer-readable storage medium, the storage medium storing computer instructions, and when the computer reads the computer instructions in the storage medium, the computer executes a creep stage determination method for an aluminum-containing heat-resistant alloy furnace tube.

When describing the operations performed in the embodiments of the present disclosure in terms of the steps, the order of the steps is all interchangeable if not otherwise indicated, the steps may be omitted, and other steps may be included in the process of operation.

The embodiments in the present disclosure are for the purpose of exemplification and illustration only and do not limit the scope of application of the present disclosure. For a person skilled in the art, various corrections and alterations that may be made under the guidance of the present disclosure remain within the scope of the present disclosure.

Some features, structures, or characteristics of one or more embodiments of the present disclosure may be suitably combined.

What is claimed is:

1. A creep stage determination method for an aluminum-containing heat-resistant alloy furnace tube at a temperature of 1100° C., comprising:
S1, performing microstructural observation and analysis at a 1/4-3/4 wall thickness part of a cross-section of the aluminum-containing heat-resistant alloy furnace tube, including:
measuring an area S1 of a peripheral lumpy precipitate $M_{23}C_6$-type carbide in an austenitic grain boundary precipitate of a furnace tube material within a field-of-view area $S_0$, and determining an area fraction of the area $S_1$ of the peripheral lumpy precipitate $M_{23}C_6$-type carbide in the austenitic grain boundary precipitate to the field-of-view area $S_0$ as $A=S_1/S_0\times100\%$, with a unit of 1;
measuring an area $S_2$ of an internal thin strip-like precipitate $M_7C_3$-type carbide in the austenitic grain boundary precipitate of the furnace tube material within the field-of-view area $S_0$, and determining an area fraction of the area $S_2$ of the internal thin strip-like precipitate $M_7C_3$-type carbide in the austenitic grain boundary precipitate to the field-of-view area $S_0$ as $B=S_2/S_0\times100\%$, with a unit of 1; and
measuring an aspect ratio C of the internal thin strip-like precipitate $M_7C_3$-type carbide in the austenitic grain boundary precipitate of the furnace tube material within the field-of-view area $S_0$, with a unit of 1;
S2, determining an influence function of a creep stage of the aluminum-containing heat-resistant alloy furnace tube at 1100° C. based on the area fractions A and B and the aspect ratio C:

$$f(A,B,C)=[(aA+bB+cC)/100]\times100\%$$

where a is 1200, b is −10, and c is −0.3;
S3, dividing the creep stage of the aluminum-containing heat-resistant alloy furnace tube at 1100° C., including:
if f(A,B,C)≤10%, determining a creep state of a 27Cr44Ni5W3Al+microalloyed furnace tube as a creep first stage;
if 10%<f(A,B,C)≤30%, determining the creep state of the 27Cr44Ni5W3Al+microalloyed furnace tube as an early phase of the creep second stage;
if 30%<f(A,B,C)≤70%, determining the creep state of the 27Cr44Ni5W3Al+microalloyed furnace tube as a mid-phase of the creep second stage; and
if 70%<f(A,B,C)≤90%, determining the creep state of the 27Cr44Ni5W3Al+microalloyed furnace tube as an end phase of the creep second stage.

2. The creep stage determination method of claim 1, wherein the microstructural observation is performed using an Olympus® GX53 metallurgical microscope with a magnification of 1,000 times; and
no fewer than 20 fields of view are randomly selected fro each specimen for the microstructure observation.

3. The creep stage determination method of claim 1, wherein microstructure analysis of microstructure photographs is performed using an Image Pro® Plus 6.0 image analysis software, and measurement data is an arithmetic mean of all fields of view measurements.

4. The creep stage determination method of claim 3, wherein when using the Image Pro® Plus 6.0 image analysis software to perform the microstructure analysis of the microstructure photographs, regions are selected with a range of 10, a thresh of 3, a smooth of 1, and a speed of 2.

5. The creep stage determination method of claim 1, wherein an austenite grain boundary and intragranular total precipitate of the furnace tube material comprises the $M_{23}C_6$-type carbide, the $M_7C_3$-type carbide, and a $Ni_3Al$ phase.

6. The creep stage determination method of claim 1, wherein the aluminum-containing heat-resistant alloy furnace tube is the 27Cr44Ni5W3Al+microalloyed furnace tube.

* * * * *